United States Patent [19]

Roberts et al.

[11] Patent Number: 4,891,444

[45] Date of Patent: Jan. 2, 1990

[54] OXA-ORGANIC SULFUR COMPOUNDS, THEIR PREPARATION AND USE

[75] Inventors: John S. Roberts; Tod K. Shioyama, both of Bartlesville, Okla.

[73] Assignee: Phillips Petroleum Company, Bartlesville, Okla.

[21] Appl. No.: 234,315

[22] Filed: Aug. 19, 1988

[51] Int. Cl.$^4$ .................. C07C 148/00; C07C 149/14
[52] U.S. Cl. ........................... 568/44; 568/49; 568/50; 568/62; 204/157.6
[58] Field of Search .................. 568/62, 44, 49, 50

[56] References Cited

U.S. PATENT DOCUMENTS 2,522,589  9/1950  Vaughan et al. .............. 204/157.78
3,050,452  8/1962  Louthan .............................. 204/162

Primary Examiner—John F. Niebling
Assistant Examiner—David G. Ryser
Attorney, Agent, or Firm—Laney, Dougherty, Hessin & Beavers

[57] ABSTRACT

Oxa-organic sulfur compounds, methods of preparing such compounds and methods of using the compounds as polymer chain length terminating agents are provided. The compounds are prepared by reacting allyl alcohol in the presence of a basic catalyst with a compound having the formula

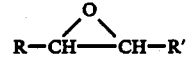

to form an intermediate. The intermediate is then reacted with hydrogen sulfide in the presence of ultraviolet radiation and a trialkyl phosphite to form the oxa-organic sulfur compound having the formula

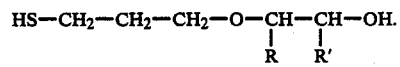

4 Claims, No Drawings

OXA-ORGANIC SULFUR COMPOUNDS, THEIR PREPARATION AND USE

BACKGROUND OF THE INVENTION

1. Field of the Invention

The present invention relates to novel oxygen-containing organic sulfur compounds, methods of preparing such compounds and methods of using the compounds as polymer chain length terminating agents.

2. Description of the Prior Art

In the synthesis of a polymer from monomer reactants, the average chain length, and hence the average molecular weight, has heretofore been controlled at a desired level by combining a chain length terminating agent with the reaction mixture during the course of the reaction. The chain length terminating agent is a compound which is more reactive than the monomer reactants, but which does not self-polymerize or copolymerize with the monomers. When introduced into the polymer synthesis reaction mixture, the chain length terminating agent preferentially reacts with the then-existent polymer chains to cause the termination of additional chain growth. Heretofore unavailable highly reactive oxygen-containing organic sulfur compounds are particularly suitable as polymer chain length terminating agents.

The preparation of organic sulfur compounds by reacting hydrogen sulfide with organic compounds containing ethylenic linkages has heretofore been known in the art. For example, U.S. Pat. No. 3,050,452, issued Aug. 21, 1962, describes the preparation of organic sulfur compounds such as mercaptans and thioethers by reacting an ethylenically unsaturated compound with hydrogen sulfide in the presence of ultraviolet radiation and a trialkyl phosphite promoter.

By the present invention novel oxa-organic sulfur compounds, methods of preparing such compounds and methods of using the compounds as polymer chain length terminating agents are provided.

SUMMARY OF THE INVENTION

The novel oxa-organic sulfur compounds of this invention have the structural formula

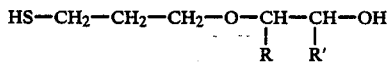

wherein R is an alkyl or aryl group containing a halide, nitro, sulfide or ether substituent and R' is hydrogen or an alkyl or aryl group containing a halide, nitro, sulfide or ether substituent.

The compounds are prepared by reacting allyl alcohol ($CH_2=CH-CH_2-OH$) in the presence of a base with an oxygen-containing compound of the structural formula

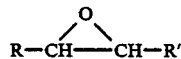

to form an intermediate of the formula

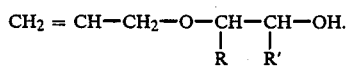

The intermediate is then reacted with hydrogen sulfide in the presence of ultraviolet radiation and trialkyl phosphite.

As previously indicated, the oxa-organic sulfur compounds are particularly suitable for use as polymer chain length terminating agents. In such use, the average chain length of a polymer during the synthesis thereof from monomer reactants is controlled by combining an oxa-organic sulfur compound of this invention with the reaction mixture during the course of the synthesis reaction.

It is, therefore, a general object of the present invention to provide novel oxa-organic sulfur compounds.

A further object of the present invention is the provision of methods of preparing novel oxa-organic sulfur compounds.

Yet a further object of the present invention is the provision of methods of controlling the average chain length of a polymer during the synthesis thereof from monomer reactants.

Other objects, features and advantages of the present invention will be readily apparent to those skilled in the art upon a reading of the description of preferred embodiments which follows.

DESCRIPTION OF PREFERRED EMBODIMENTS

Oxa-organic sulfur compounds are provided having the structural formula

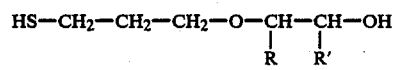

wherein R is an alkyl or aryl group containing a halide, nitro, sulfide or ether substituent and R' is hydrogen or an alkyl or aryl group containing a halide, nitro, sulfide or ether substituent. An example of one such novel compound is 6-mercapto-2-methyl-3-oxa-1-hexanol (R is $-CH_3$ and R' is $-H$.) which has the structural formula $$HS-CH_2-CH_2-CH_2-O-CH-CH_2-OH.$$
$$\hspace{3.5cm} |$$
$$\hspace{3.5cm} CH_3$$

Another example is 2-chloromethyl-6-mercapto-3-oxa-1-hexanol (R is $-CH_2Cl$ and R' is -H) which has the structural- formula

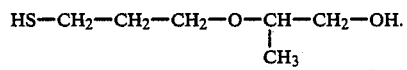

Yet another such oxa-organic sulfur compound is 2-butyl-6-mercapto-3-oxa-1-hexanol (R is $-CH_2-CH_2-CH_2-CH_3$ and R' is $-H$) which has the structural formula

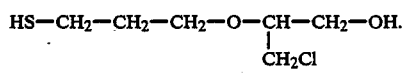

The oxa-organic sulfur prepared by first reacting allyl alcohol ($CH_2=CH-CH_2-OH$) in the presence of a base catalyst with a compound having the formula

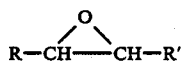

where R is an alkyl or aryl group containing a halide, nitro, sulfide or ether substituent and R' is hydrogen or an alkyl or aryl group containing a halide, nitro, sulfide or ether substituent, to form an intermediate of the formula

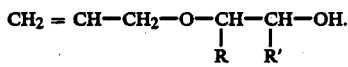

Examples of the starting oxygen-containing organic compounds are propylene oxide (R is —CH$_3$ and R' is —H), epichlorohydrin (R is —CH$_2$Cl and R' is —H), n-butyloxiran (R is —CH$_2$—CH$_2$—CH$_2$—CH$_3$ and R' is —H) and other epoxides.

The first reaction is carried out at a temperature in the range of from about 90° C. to 160° C. and a pressure of from 0 to about 200 psig. Preferably, the reaction is conducted at a temperature in the range of from about 100° C. to about 150° C., most preferably from about 100° C. to about 140° C., and at a pressure in the range of from about 10 psig to about 150 psig.

Any base which does not interfere with the reaction can be used as a catalyst. Examples of suitable bases are Periodic Table Group I metal hydroxides or amides, Periodic Table Groups I and II metal phenoxides and alkyl lithium, sodium and potassium compounds. Specific examples are lithium hydroxide, potassium hydroxide, barium phenoxide, calcium phenoxide, sodium amide, and n-butyl lithium. The base can advantageously be used in an alcohol solution, e.g., 20% by weight sodium hydroxide in methanol.

The amount of catalyst utilized can vary from about $10^{-4}$ to 1 mole of catalyst per mole of oxygen-containing organic compound. A preferred catalyst amount is in the range of from about $10^{-3}$ to 0.1 mole of catalyst per mole of oxygen-containing organic compound with the most preferred range being from about 0.005 to about 0.05 mole of catalyst per mole of oxygen-containing organic compound.

The mole ratio of allyl alcohol to oxygen-containing organic compound utilized can vary from about 0.25 to about 10. A preferred mole ratio of allyl alcohol to oxygen-containing organic compound is from about 0.5 to about 6, with the most preferred range being from about 0.75 to about 3.

When the oxygen-containing organic compound is propylene oxide, the allyl alcohol and base catalyst, e.g., a 20% by weight solution of sodium hydroxide in methanol, are preferably combined and heated in a reaction chamber to a temperature of about 110° C. The propylene oxide is then added to the reaction chamber under pressure between about 10 psig and about 70 psig while maintaining the temperature in the range of from about 110° C. to about 140° C. The pressure in the reaction chamber is increased with nitrogen at the end of the reaction to about 150 psig to force any unreacted propylene oxide into the alcohol solution. The intermediate reaction product, i.e., 2-methyl-3-oxa-5-hexen-1-ol having the formula

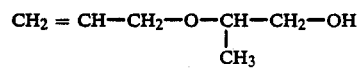

is separated from unreacted reactants, alcohol, etc., by distillation.

The intermediate obtained in the first reaction is reacted with hydrogen sulfide in a second reaction in the presence of ultraviolet radiation and a trialkyl phosphite, preferably tri-n-butyl phosphite. The second reaction can be carried out at any desired temperature and corresponding pressure so long as the pressure limitation of the ultraviolet reactor is not exceeded, generally a pressure of about 500 psig. A reaction temperature in the range of from about −50° C. to about 100° C. usually results in reaction pressure levels below about 500 psig.

Any suitable source of radiation providing wavelengths in the ultraviolet range can be used. The reaction vessel should be transparent to such ultraviolet radiation and can be formed of such materials as Pyrex, Vycor and quartz. Ultraviolet radiations having wave lengths in the range of 100 to 3800 Angstrom units are suitable with wave lengths below about 2900 Angstrom units being preferred. Generally, the rate of ultraviolet radiation expressed in terms of rep. (roentgen equivalent physical) per hour will be in the range between $1 \times 10^3$ to $1 \times 10^{10}$.

The organic trialkyl phosphite catalyst is of the general formula (RO)$_3$P wherein R is an alkyl radical having from 1 to about 10 carbon atoms. Examples of such trialkyl phosphite catalysts are trimethyl phosphite, triethyl phosphite, tripropyl phosphite, tributyl phosphite and tripentyl phosphite with tributyl phosphite being the most preferred. The trialkyl phosphite catalyst is utilized in a quantity within the range of from about $1 \times 10^{-6}$ to about 0.10 mole of catalyst per mole of intermediate compound.

The mole ratio of hydrogen sulfide to intermediate compound can vary from about 0.25 to about 15. A preferred mole ratio of hydrogen sulfide to intermediate is from about 0.5 to about 10 with from about 3 to about 6 being the most preferred.

When the 2-methyl-3-oxa-5-hexen-1-ol intermediate formed from propylene oxide and allyl alcohol is reacted with hydrogen sulfide, the intermediate and tributyl phosphite catalyst are preferably added to an ultraviolet reactor at room temperature. Hydrogen sulfide is charged to the reactor and the reaction is carried out at a pressure in the range of from about 230 psig to about 250 psig and a temperature in the range of from about 26° C. to about 30° C. in the presence of ultraviolet radiation. The resultant product, i.e., 6-mercapto-2-methyl-3-oxa-1-hexanol is separated from unreacted components by distillation. The overall yield of product from the reactions is typically from about 30% to about 40%.

While the novel oxa-organic sulfur compounds of this invention have other potential uses such as in the synthesis of adhesive compositions, they are particularly suitable as polymer chain length terminating agents. In such use, an oxa-organic sulfur compound is combined with the reaction mixture of monomers and synthesizing polymer during the synthesis reaction of a polymer so that the more reactive oxaorganic sulfur compound reacts with polymer chains in the mixture and thereby terminates further polymer chain growth. The use of one type of chain terminating compound over another depends on the reactivity of the compound as well as its solubility in the particular polymer synthesis reaction mixture involved. The oxa-organic sulfur compounds of this invention are most suitable for use as polymer chain length terminating agents in the syntheses of acrylic polymers, polyvinyl chloride polymers, styrene-butadiene polymers and neoprene polymers. Generally, the oxa-organic sulfur compound is combined with the polymer synthesis reaction mixture in an amount of about $1 \times 10^{-8}$ to about $1 \times 10^{-2}$ times the quantity of monomer originally present therein to cause the termination of polymer chain growth.

In order to illustrate the invention further, the following example is given.

EXAMPLE 6000 grams (103.4 moles) of allyl alcohol were reacted with 4000 grams (69.0) moles of propylene oxide in the presence of 69 grams of a 20% by weight sodium hydroxide in methanol solution (0.005 moles sodium hydroxide/mole propylene oxide). After adding the allyl alcohol and sodium hydroxide-methanol solution to a 5-gallon reactor, the reactor was heated to 125° C. The propylene oxide was placed in an ancillary vessel and pressured into the reactor with nitrogen gas while continuously stirring the reactor contents. The propylene oxide was added in stages by pressure increases of 10 to 20 psig. During the addition, the temperature was held at about 125° C. and the pressure varied between about 50 psig and 115 psig. After all of the propylene oxide was added, the reaction mixture was held at a temperature of 125° C. and a pressure of about 90 psig for about one hour.

The crude intermediate reaction mixture containing 2-methyl-3-oxa-5-hexen-1-ol intermediate compound was transferred to a distillation flask and distilled in a large stainless steel packed column. 6088.8 grams of the 2-methyl-3-oxa-5-hexen-1-ol intermediate compound were recovered. The yield was 76.1%.

2683 grams (29.2 moles) of the intermediate compound, 2-methyl-3-oxa-5-hexen-1-ol were reacted in equal portions in two runs in a large ultraviolet reactor. 3.65 grams (0.0146 mole) of tributyl phosphite promoter were added to the reactor in the first run and 36.5 grams (0.146 mole) of tributyl phosphite were added in the second run. 1490 grams (43.8 moles) of hydrogen sulfide were pressured into the reactor in each run. In each run, the reactions proceeded with ultraviolet radiation and stirring at temperatures in the range of from about 26° C. to 29° C. and pressures in the range of from about 230 psig to about 250 psig. The crude reaction products obtained contained 63.26% and 57.2%, respectively, 6-mercapto-2-methyl-3-oxa-1-hexanol. The crude reaction mixtures from the two runs were combined, transferred to a distillation flask and distilled in a large stainless steel packed column. The distillation resulted in the recovery of 1886.7 grams of 6-mercapto-2-methyl-3-oxa-1-hexanol. The yield was 43.1%.

Thus, the present invention is well adapted to attain the ends and advantages mentioned as well as those inherent therein. While numerous changes in reactants, reaction conditions and procedures followed may suggest themselves to those skilled in the art, such changes are encompassed within the spirit of the invention as defined by the appended claims.

What is claimed is:

1. An oxa-organic sulfur compound having the structural formula

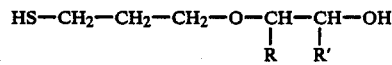

wherein R is an alkyl or aryl group containing a halide, nitro, sulfide or ether substituent and R' is hydrogen or an alkyl or aryl group containing a halide, nitro, sulfide or ether substituent.

2. The compound of claim 1 wherein R is —CH$_3$ and R' is —H.

3. The compound of claim 1 wherein R is —CH$_2$Cl and R' is —H.

4. The compound of claim 1 wherein R is —CH$_2$—CH$_2$—CH$_2$—CH$_3$ and R' is —H.

* * * * *

UNITED STATES PATENT AND TRADEMARK OFFICE
CERTIFICATE OF CORRECTION

PATENT NO. : 4,891,444
DATED : January 2, 1990
INVENTOR(S) : John S. Roberts; Tod K. Shioyama It is certified that error appears in the above-identified patent and that said Letters Patent is hereby corrected as shown below:

Column 2, line 66, after sulfur, insert --compounds are--.

Signed and Sealed this

Twenty-ninth Day of January, 1991

Attest:

HARRY F. MANBECK, JR.

Attesting Officer      Commissioner of Patents and Trademarks